(12) United States Patent
Lidgren

(10) Patent No.: US 7,883,481 B2
(45) Date of Patent: *Feb. 8, 2011

(54) DEVICE FOR MINI-INVASIVE ULTRASOUND TREATMENT OF DISC DISEASE

(75) Inventor: Lars Åke Alvar Lidgren, Lund (SE)

(73) Assignee: Ultrazonix DNT AB, Limhamn (SE)

( * ) Notice: Subject to any disclaimer, the term of this patent is extended or adjusted under 35 U.S.C. 154(b) by 618 days.

This patent is subject to a terminal disclaimer.

(21) Appl. No.: 10/333,161

(22) PCT Filed: Jul. 16, 2001

(86) PCT No.: PCT/SE01/01626

§ 371 (c)(1),
(2), (4) Date: Mar. 11, 2003

(87) PCT Pub. No.: WO02/05897

PCT Pub. Date: Jan. 24, 2002

(65) Prior Publication Data

US 2003/0163067 A1  Aug. 28, 2003

(51) Int. Cl.
*A61N 7/00* (2006.01)
(52) U.S. Cl. .......................................... 601/2
(58) Field of Classification Search ............ 601/4, 601/2, 3; 607/96, 108, 109, 115–117, 105; 600/426, 427, 549, 41, 49
See application file for complete search history.

(56) References Cited

U.S. PATENT DOCUMENTS

| | | | |
|---|---|---|---|
| 5,150,712 A | | 9/1992 | Dory |
| 5,295,483 A | * | 3/1994 | Nowacki et al. ............ 600/439 |
| 5,433,739 A | | 7/1995 | Sluijter et al. |
| 5,443,068 A | | 8/1995 | Cline et al. |
| 5,471,988 A | * | 12/1995 | Fujio et al. .................. 600/439 |
| 5,485,839 A | * | 1/1996 | Aida et al. ................... 600/427 |
| 5,526,814 A | * | 6/1996 | Cline et al. .................. 600/411 |
| 5,769,790 A | | 6/1998 | Watkins et al. |
| 6,071,238 A | | 6/2000 | Chapelon et al. |

(Continued)

FOREIGN PATENT DOCUMENTS

EP  0872262  10/1998

*Primary Examiner*—Brian Casler
*Assistant Examiner*—Elmer Chao
(74) *Attorney, Agent, or Firm*—Ladas & Parry LLP

(57) ABSTRACT

Device for miniinvasive ultrasound treatment of disc disease. A therapeutic ultrasound tranducer (2) is provided for treatment of the disc (5), of a patient (4) by generating an ultrasonic field (3), of which the temperature focus (F) is located in the disc (5), for heating thereof. The device comprises an optical navigating device (20) with a signal receiving or signal sending unit (32). A reference device (28) has a set position relative to the disc (5). The Therapeutic ultrasound transducer (2) is provided for insertion through the skin of the patient (4) and engagement of the disc (5), preferably anulus fibrosus (8), and it has a flexible wall with an ultrasound transmitting element provided within the flexible wall. Between the flexible wall and the ultrasound transmitting element there is located at least one cooling chamber (11) with cooling liquid for cooling the ultrasound transmitting element and the tissue closest to the therapeutic ultrasound transducer (2) and a temperature sensor is provided to measure the temperature in the disc (5), preferably anulus fibrosus (8).

17 Claims, 3 Drawing Sheets

U.S. PATENT DOCUMENTS

Figure 1:
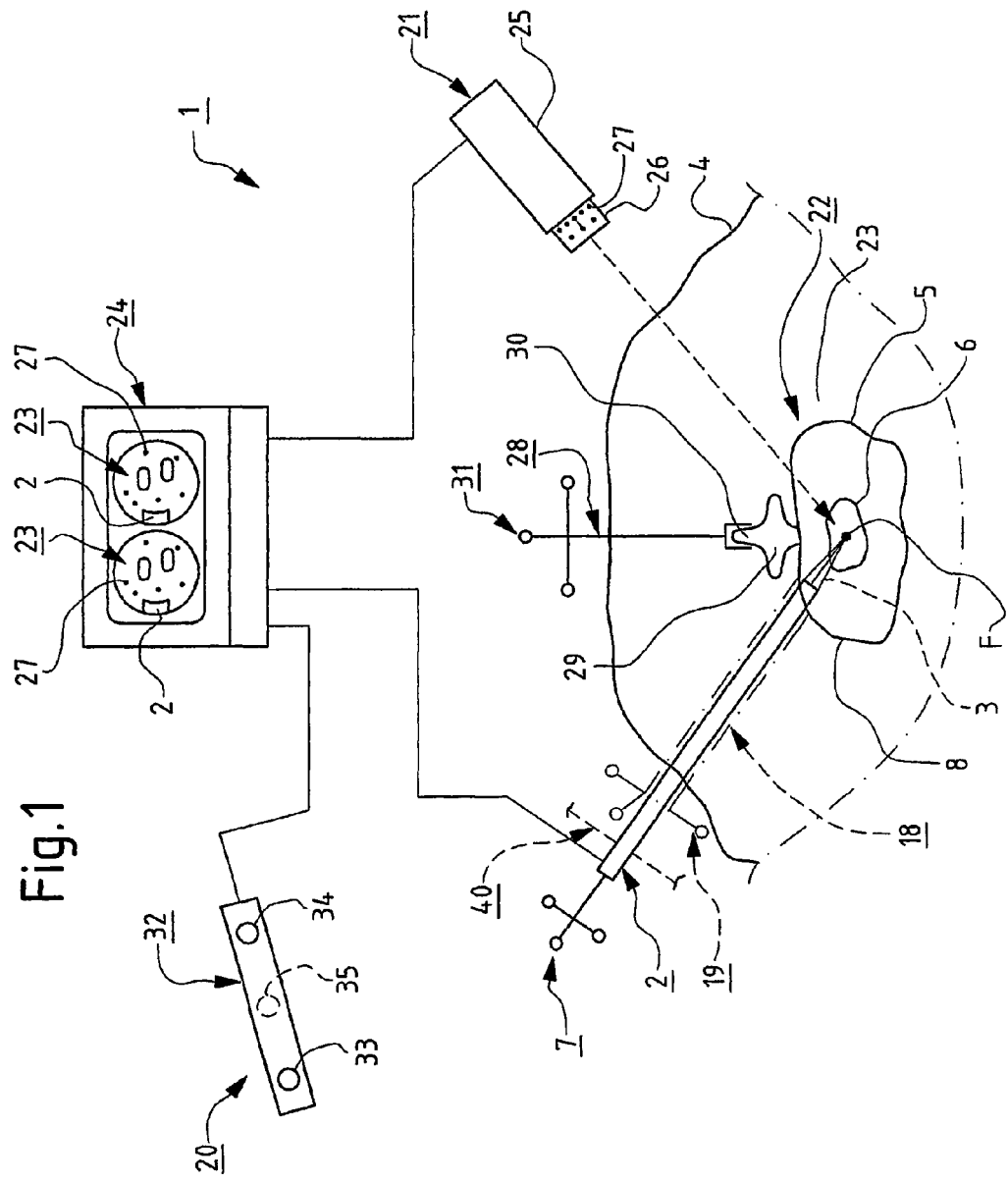

| | | | |
|---|---|---|---|
| 6,073,051 A * | 6/2000 | Sharkey et al. | 607/99 |
| 6,226,548 B1 * | 5/2001 | Foley et al. | 600/426 |
| 6,254,553 B1 * | 7/2001 | Lidgren et al. | 601/3 |
| 6,311,540 B1 * | 11/2001 | Paltieli et al. | 73/1.82 |
| 6,511,444 B2 * | 1/2003 | Hynynen et al. | 601/2 |
| 6,547,810 B1 * | 4/2003 | Sharkey et al. | 607/96 |
| 6,905,509 B2 * | 6/2005 | Dobak et al. | 607/96 |
| 2003/0069569 A1 * | 4/2003 | Burdette et al. | 606/27 |
| 2003/0130576 A1 * | 7/2003 | Seeley et al. | 600/426 |

* cited by examiner

DEVICE FOR MINI-INVASIVE ULTRASOUND TREATMENT OF DISC DISEASE

BACKGROUND OF THE INVENTION

1. Field of the Invention

The present invention relates to a device for mini-invasive ultrasound treatment of disc disease, wherein at least one therapeutic ultrasound transducer is provided for treatment of the disc, preferably nucleus pulposus, of a patient by generating by means of said therapeutic ultrasound transducer an ultrasonic field, the temperature focus of which is located in the disc, preferably nucleus pulposus, for heating thereof.

2. Description of the Related Art

The intervertebral disc consists of an outer fibrous tissue ring, anulus fibrosus, and an inner, more viscous part, nucleus pulposus. The disc functions as a shock absorber and if anulus fibrosus breaks, e.g. a small fissuring, disc matter may find its way out and cause a compression of nerve roots and induce an inflammatory reaction.

Prolapsed intervertebral discs have been treated surgically since the thirties by removal of the displaced disc matter and/or a part of the bulging disc. Later, the surgical treatment has developed towards less invasive operations and now, microscopes and percutaneous techniques are used for removing disc matter. An alternative method for surgical treatment is chemonucleolys, where the enzyme chymopapain is injected into nucleus pulposus, the central part of the disc. The enzyme polymerizes the long proteoglycan chains in nucleus pulposus with subsequent loss of the hygroscopicity. This reduces the volume and pressure in nucleus pulposus and the bulging part of the disc, which explains the pain relief patients with sciatica experience after chemonucleolys. The method has proven to give pain relief in 75 per cent of the cases and has a well documented cost efficiency. Unfortunately, the method has caused serious allergic reactions in about 1 per cent of the cases. Next step in the development could be a non-invasive treatment or therapy of prolapsed intervertebral discs, which preferably should be painless, avoid the risk for infections and carried through ambulatory.

A method for thermotherapy and coagulation of tissue involves use of focused ultrasound with high intensity. The ultrasound pass well through soft tissue and can be focused on remote spots within a surface of a few millimeters. The energy absorption in the tissue increases the temperature with a sharp temperature gradient such that the boundaries of the treated volume are clearly limited without causing any damages on the surrounding tissue (U.S. Pat. Nos. 5,291,890, 5,501,655). Ultrasound treatment or therapy of prolapsed intervertebral discs is previously known (EP 0 872 262).

Heat treatment or thermotherapy of discs has proven successful in a method called IDET (U.S. Pat. Nos. 6,073,051, 6,007,570, 5,980,504). The method has as its aim to insert a catheter into the disc by means of a cannula. Farthest out on the catheter there is a spool which is heated by applying a radio frequency voltage thereon (U.S. Pat. No. 5,785,705). The heat is increased to about 90° C. in nucleus pulposus where the heating element of the catheter has been located and treatment or therapy is carried through for about 15 minutes.

Surgery with focused ultrasound has several advantages compared with other thermal techniques. In the first place, it is non-invasive, secondly, focus can be made movable and thirdly, the energy can be supplied in a few seconds. The limitation of ultrasound is its absorption in bone and its poor penetration through gas-filled passages. Clinical applications of ultrasound surgery are today mostly used in ophtalmic surgery, urology and oncology. The effect of ultrasound can be divided into thermal and non-thermal effects.

The thermal effects of ultrasound are caused by absorption of ultrasound in the tissue. This leads to a temperature increase which is dependent on the parameters of the ultrasound (frequency and intensity) and the acoustic properties of the tissue. The absorption of ultrasound in musculoskeletal tissues increases with the apatite and protein content, which means high absorption in bone, cartilage, tendons and ligaments. Water however, has a low ultrasound absorption capacity and can for this reason be used as an acoustic medium between the ultrasound transducer and the tissue. Higher absorption can be expected in anulus fibrosus (high collagen content) than in nucleus pulposus (high water content). This will lead to higher temperatures in the outer part of the intervertebral disc than in the central part. In order to avoid that the temperature in anulus fibrosus exceeds a detrimental level at the same time as the temperature in nucleus pulposus reaches a sufficient level, the ultrasound can be transmitted from several ultrasound sources. In this manner, the fields will overlap each other and increase the effect in nucleus pulposus at the same time as the intensity in the surrounding tissue including anulus fibrosus can be kept low.

BRIEF SUMMARY OF THE INVENTION

The object of the present invention has been to facilitate, at the abovementioned devices, location of the temperature focus of the ultrasonic field of the ultrasound transducer on a desired point in the disc, preferably in nucleus pulposus. This is arrived at according to the invention by means of a device having the characterizing features of subsequent claim 1.

By means of the device defined in the claims, it is achieved that the temperature focus of the ultrasonic field of the therapeutic ultrasound transducer can be located and maintained on the desired point in the disc, preferably in nucleus pulposus.

BRIEF DESCRIPTION OF THE DRAWING FIGURES

Figure 2:
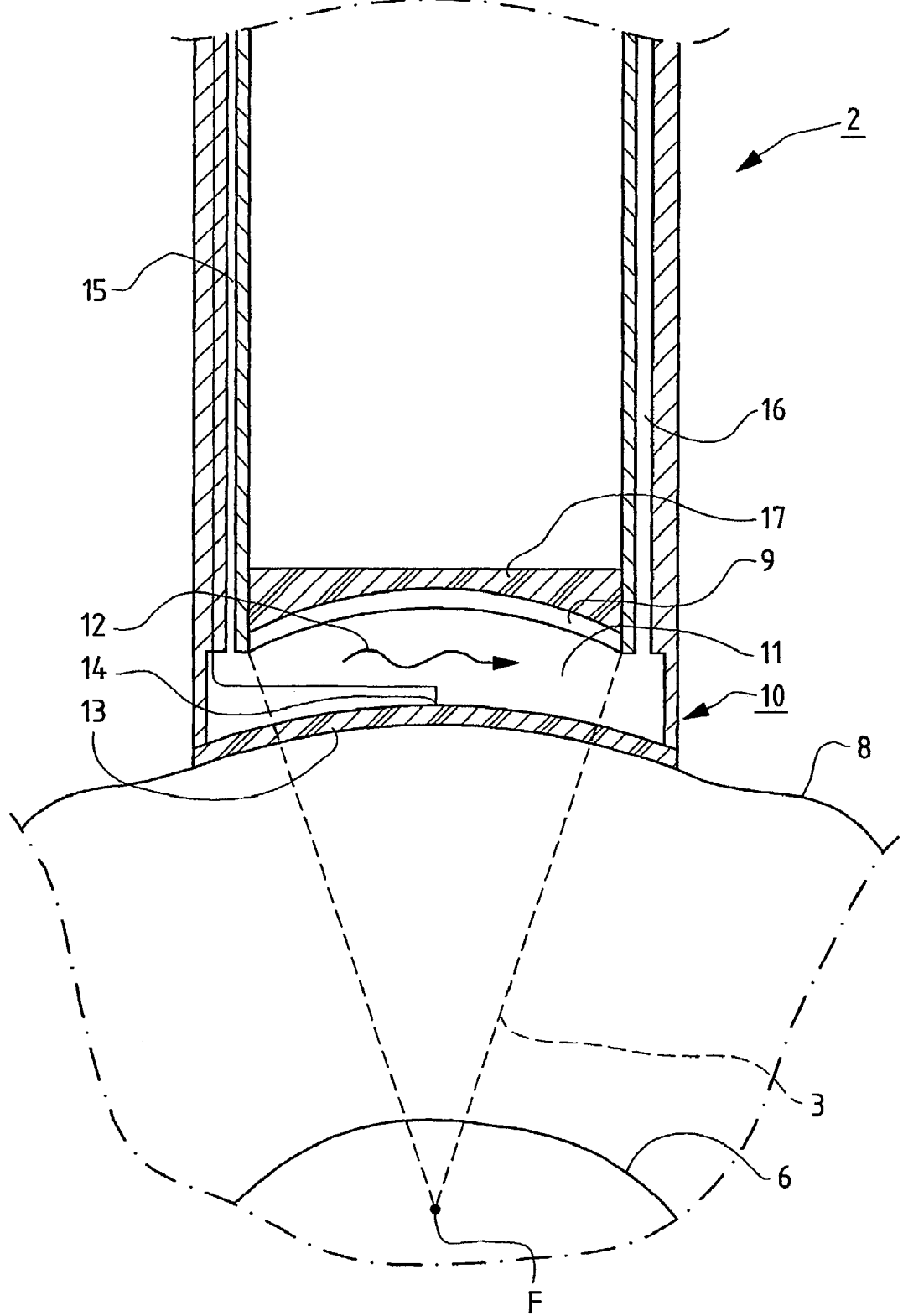
Figure 3:
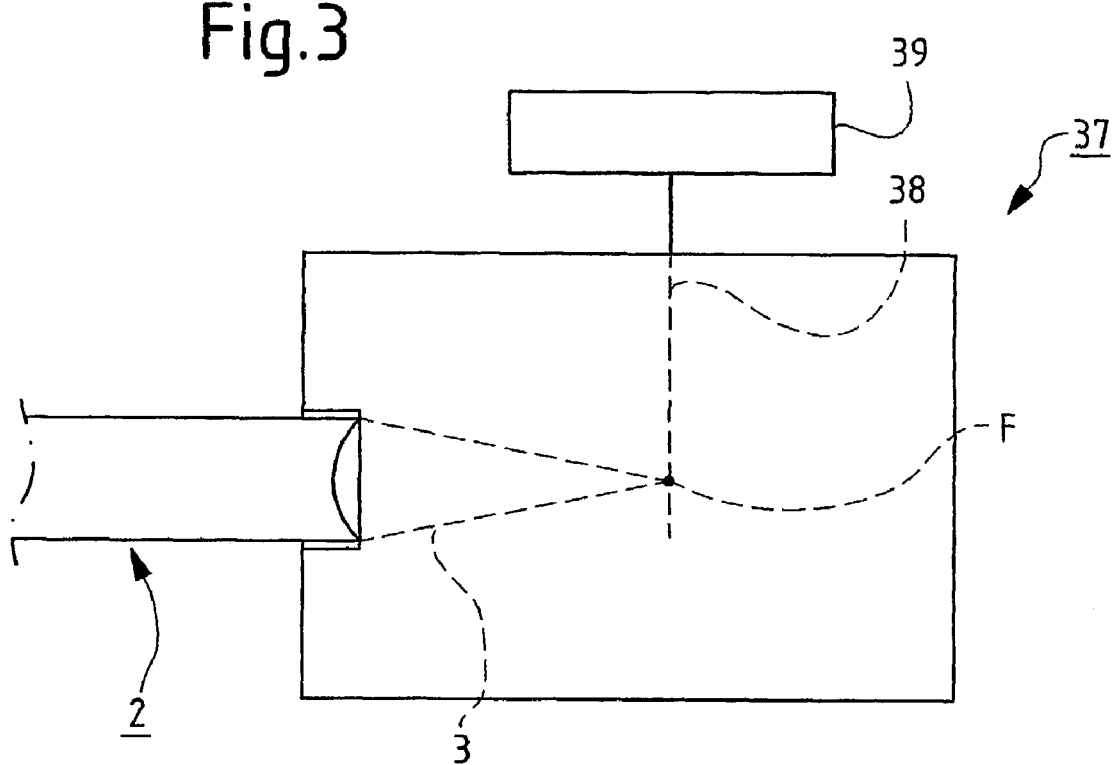

The invention will be further described below with reference to the accompanying drawings, in which FIG. 1 schematically illustrates a structural embodiment of the device according to the invention;

FIG. 2 schematically illustrates a therapeutic ultrasound transducer forming part of the device according to FIG. 1; and FIG. 3 schematically illustrates a calibrating device which may form part of a device according to FIG. 1.

DETAILED DESCRIPTION OF THE PREFERRED EMBODIMENTS

The treatment device 1 schematically illustrated in FIG. 1 is adapted to generate, by means of a therapeutic ultrasound transducer 2 (so called therapeutic transducer), an ultrasonic field 3, the temperature focus F of which is intended to be located in the intervertebral disc 5, preferably in nucleus pulposus 6, of the patient 4 for treatment thereof. The therapeutic ultrasound transducer 2 comprises a plurality of, preferably three or more position transmitters 7 for determining its position.

The therapeutic ultrasound transducer 2 is adapted to be inserted through the patient's 4 skin and engage the disc 5, preferably anulus fibrosus 8, to provide a local temperature increase in nucleus pulposus 6 so that enzymes such as collagenase present in the disc are activated and cause decomposition of collagen and proteoglycanes, which results in shrinking of nucleus pulposus 6 primarily because of less hygroscopicity. The therapeutic ultrasound transducer 2 can be placed against the disc 5 without perforating anulus fibrosus 8 and thereby transmit the ultrasonic field 3 focused in temperature focus F towards the treatment volume. The transmitter element 9 of the therapeutic ultrasound transducer 2, e.g. a piezoelectric element, may be cooled with water for cooling the crystal and the tissue closest to the therapeutic ultrasound transducer 2 in a similar way as one today does in microwave therapy of cancer in the prostate gland (U.S. Pat. No. 5,964,791).

In order to provide said cooling, the therapeutic ultrasound transducer 2 is provided at its distal end 10 with at least one cooling chamber 11 with cooling liquid 12. This cooling chamber 11 is located between the transmitter element 9 and a membrane-like wall 13 of such flexible material that said wall is able to adapt to the surface of anulus fibrosus 8 when it is brought in contact therewith.

The therapeutic ultrasound transducer 2 further comprises at least one temperature sensor 14 for measuring the temperature before and/or during treatment. In order to increase the volume of therapy or treatment, the direction or setting of the therapeutic ultrasound transducer 2 can be varied such that temperature focus F is scanned over a larger area. The temperature sensor 14 is provided to measure the temperature at the inner side of the flexible wall 13 and it is preferably connected to said wall 13 such that it follows the wall 13 when said wall is deformed when brought in contact with the surface of anulus fibrosus 8.

The cooling liquid 12 is preferably water which is distributed through an inlet passage 15 to the cooling chamber 11 and through an outlet passage 16 therefrom such that the water can circulate through the cooling chamber 11. A sealing means 17 is provided within the transmitter element 9 for preventing cooling liquid 12 from finding its way out of the cooling chamber 11.

In more detail, the therapeutic ultrasound transducer 2 is adapted to cause a local temperature increase in nucleus pulposus 6 so that enzymes such as collagenase present in the disc 5, are activated and cause decomposition of collagen and proteoglycanes, which results in shrinking of nucleus pulposus 6 primarily because of less hygroscopicity.

The treatment device 1 may comprise a rigid tube 18 with associated inner portion and several position transmitters 19, preferably three such transmitters. The tube 18 may, by means of optical navigation technique, be inserted dorsolaterally towards the disc 5. The inner portion of the tube 18 is then replaced by the therapeutic ultrasound transducer 2 and said tube 18 is schematically illustrated in FIG. 1 with broken lines.

The treatment device 1 also comprises an optical navigating device 20 to navigate the therapeutic ultrasound transducer 2 (U.S. Pat. No. 5,772,594). This optical navigating device 20 comprises at least one diagnostic camera 21 which is adapted to produce at least one picture or image of the anatomic structure 23 of the treatment area 22 in a monitor 24. The diagnostic camera 21 may be an X-ray camera 25 taking two pictures of the anatomic structure 23 of the treatment area 22 from different directions with preferably a 90° intermediate angle and showing or displaying these in the monitor 24. At the optical navigating device 20, the X-ray camera 25 is used together with an optical analogue-digital-converter for obtaining or producing a real time image or picture in the monitor 24 of the position and direction of the therapeutic ultrasound transducer 2 (U.S. Pat. Nos. 6,021,343, 5 834 759, 5,383,454).

The X-ray camera 25 comprises a calibrating device 26—e.g. a calibrating hood—which is located in front of the objective of the X-ray camera 25 and having markers 27 the mutual distances of which are known. The markers 27 may be round and consist e.g. of tantalum.

The optical navigating device 20 further comprises a reference device 28 which is provided to be attached to the spinous process 30 of a vertebra 29 or in a corresponding position such that it gets a determined or fixed position relative to the treatment area 22. The reference device 28 has several position transmitters 31, namely preferably at least three, and these may consist of metallic material, e.g. tantalum.

Furthermore, the optical navigating device 20 comprises a signal receiving and/or signal sending unit 32. This includes a suitable number of signal receivers 33, 34 for receiving reflected or other signals from the position transmitters 7 and 31 of the therapeutic ultrasound transducer 2 and the reference device 28 respectively. The signal receiving and/or signal sending unit 32 may eventually comprise one or more signal transmitters 35 for sending or transmitting signals to said position transmitters 7 and 31, which are provided to receive these signals.

The signals transmitted by the position transmitters 7 and 31 may e.g. be in the form of infrared light and the signal receivers 33, 34 may in such case be receivers of infrared light.

In the treatment device 1 there may also be included a calibrating unit 37 for calibrating the temperature effect of the temperature focus F of the therapeutic ultrasound transducer 2. The calibrating unit 37 has one or more thermoelements 38 by means of which the effect at said temperature focus F can be measured for calibration. The thermoelements 38 are connected to a schematically illustrated measure instrument 39.

Prior to treatment of the disc 5, preferably nucleus pulposus 6, the reference device 28 is located on the patient's 4 vertebra 29 and the therapeutic ultrasound transducer 2 is calibrated in the calibrating unit 37.

Two X-ray pictures are taken of the patient's 4 anatomic structure 23 at the disc 5 and these X-ray pictures are shown on the monitor 24. On these X-ray pictures, the position of the reference device 28 relative to the disc 5 may then be determined by means of the markers 27 of the calibrating device 26.

During treatment of the disc 5, preferably nucleus pulposus 6, the therapeutic ultrasound transducer 2 is navigated by means of the signal receiving or signal sending unit 32, whereby the navigation is presented in the X-ray pictures or images on the monitor 24. This is accomplished while the position transmitters 7 of the therapeutic ultrasound transducer 2 cooperate through signals with the signal transmitters 33, 34 of the signal receiving or signal sending unit 32. By means of said navigation, the therapeutic ultrasound transducer 2 can be positioned such that the temperature focus F of its ultrasonic field 3 will lie in the disc 5, preferably nucleus pulposus 6. The temperature in the temperature focus F preferably exceeds 45° C.

The treatment can be automatically interrupted if the patient 4 moves to an incorrect position relative to the therapeutic ultrasound transducer 2 or vice versa.

The invention is not limited to the embodiment described above, but may vary within the scope of the following claims. Thus, the treated disc 5 may e.g. be any disc in the body.

The diagnostic camera 21 may be a computerized tomography (CT) scanner which is provided to produce images of said anatomic structure 23 and these images can be processed in a computer program or software for obtaining a 3D-image in the monitor 24.

The therapeutic ultrasound transducer 2 may be provided to be positioned manually or be located on a positioning device 40 for positioning thereof relative to the disc 5 to be treated.

The invention claimed is:

1. An ultrasound treatment device comprising:
    an optical navigating device having at least one diagnostic camera that is adapted to produce at least one picture or image of an anatomic structure of a treatment area;
    at least one therapeutic ultrasound transducer adapted for insertion through the skin of a patient having a vertebral column and placement against an intervertebral disc to be treated; and having a longitudinally extending side wall and a distal end wall;
    at least one cooling chamber in which cooling liquid is provided;
    at least one ultrasound transmitting element provided at one end of the cooling chamber, where the orientation of at least one ultrasound transmitting element is substantially distally-directed, whereby the at least one ultrasound transmitting element is configured to substantially transmit through the distal end wall, and where the cooling chamber with cooling liquid is located between the at least one ultrasound transmitting element and the distal end wall and being configured to cool the ultrasound transmitting element and the tissue closest to the ultrasound transducer; and
    at least one temperature sensor provided to measure the temperature at the treatment area,
    wherein the optical navigating device further comprises at least one signal receivinq or signal sending unit, at least one position transmitter, and a reference device wherein the at least one signal receiving or signal sending unit is adapted to send signals to and receive reflected or other signals from the at least one position transmitter on:
    a) the reference device wherein the reference device has a set position relative to the disc, and
    b) the therapeutic ultrasound transducer such that the position thereof relative to said treatment area can be determined.

2. Device according to claim 1, further comprising a cooling liquid wherein the cooling liquid is circulated through the cooling chamber.

3. Device according to claim 2, wherein the cooling liquid is water.

4. Device according to claim 1, wherein the treatment area is the inner side of the distal end wall.

5. Device according to claim 4, wherein the at least one temperature sensor is connected to the distal end wall such that it follows said distal end wall during the deformation thereof when said distal end wall is brought in contact with the disc.

6. Device according to claim 1, wherein a tube with an associated inner portion is dorsolaterally insertable towards the disc and is navigatable by means of the optical navigating device and said inner portion then is replaced by the therapeutic ultrasound transducer.

7. Device according to claim 1, wherein the diagnostic camera is an X-ray camera.

8. Device according to claim 7, wherein the X-ray camera comprises a calibrating device with markers which are adapted to determine the position of the anatomic structure displayed in a monitor and present at the patient's disc.

9. Device according to claim 8, wherein the X-ray camera further comprises a monitor which is configured to display two X-ray photographs of said anatomic structure taken with the X-ray camera from two different locations.

10. Device according to claim 1, wherein the diagnostic camera is a computerized tomography (CT) scanner which is provided to produce images of the anatomic structure at the patient's disc, said images being processed in a computer program for obtaining a 3D-image in a monitor.

11. Device according to claim 1, wherein the signal receiving or signal sending unit is provided to receive or send signals in the form of infrared light, and said at least one position transmitter is configured to send or receive signals in the form of infrared light.

12. Device according to claim 1, wherein the temperature in the temperature focus of the therapeutic ultrasound transducer exceeds 45° C.

13. Device according to claim 1, wherein a calibrating device is provided for calibrating the effect emitted by the therapeutic ultrasound transducer in the temperature focus of said therapeutic ultrasound transducer and/or the position of said temperature focus relative to the ultrasound transmitting element of the therapeutic ultrasound transducer.

14. Device according to claim 1, wherein the reference device is configured to be attached to a vertebra having a spinal process in the patient's vertebral column, preferably to the spinal process of said vertebra.

15. Device according to claim 1, wherein the at least one position transmitters consist of metallic balls.

16. Device according to claim 15, wherein the at least one signal receiving or signal sending unit comprises at least one X-ray device.

17. Device according to claim 1 wherein the distal end wall is a flexible distal end wall.

* * * * *